(12) United States Patent
Zhang et al.

(10) Patent No.: US 8,815,769 B2
(45) Date of Patent: Aug. 26, 2014

(54) PROCESS FOR CONDITIONING A HIGH EFFICIENCY ETHYLENE OXIDE CATALYST

(75) Inventors: Liping Zhang, Lake Jackson, TX (US); Ravindra Radhakisan Tupe, Helsinki (FI); Ailene Gardner Phillips, Charleston, WV (US); Paul Victor Hinman, Charleston, WV (US); Hwaili Soo, Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/005,717

(22) PCT Filed: Apr. 3, 2012

(86) PCT No.: PCT/US2012/031990
§ 371 (c)(1), (2), (4) Date: Sep. 17, 2013

(87) PCT Pub. No.: WO2012/141942
PCT Pub. Date: Oct. 18, 2012

(65) Prior Publication Data
US 2014/0012022 A1 Jan. 9, 2014

Related U.S. Application Data

(60) Provisional application No. 61/473,949, filed on Apr. 11, 2011.

(51) Int. Cl.
*B01J 23/50* (2006.01)
*C07D 301/10* (2006.01)

(52) U.S. Cl.
USPC ............................................. 502/347; 549/534

(58) Field of Classification Search
CPC ...... C07D 301/10; B01J 23/50; B01J 8/0285; B01J 8/067
USPC .................... 549/534; 422/198, 652; 502/347
See application file for complete search history.

(56) References Cited

U.S. PATENT DOCUMENTS

| | | |
|---|---|---|
| 4,874,879 A | 10/1989 | Lauritzen et al. |
| 5,155,242 A | 10/1992 | Shankar et al. |
| 5,698,719 A | 12/1997 | Gaffney et al. |
| 5,856,534 A | 1/1999 | Cooker et al. |
| 7,102,022 B2 | 9/2006 | Evans et al. |
| 2007/0225511 A1 | 9/2007 | Bortinger et al. |

FOREIGN PATENT DOCUMENTS

| | | |
|---|---|---|
| EP | 0352849 A1 | 1/1990 |
| WO | 2004002971 A1 | 1/2004 |
| WO | 2004002972 A2 | 1/2004 |
| WO | 2008140714 A1 | 11/2008 |
| WO | 2008141027 A2 | 11/2008 |
| WO | 2009042300 A1 | 4/2009 |
| WO | 2011079056 A2 | 6/2011 |

OTHER PUBLICATIONS

International Search Report and Written Opinion dated, Jul. 2, 2012.
International Preliminary Examining Authority (IPEA) Written Opinion dated, Mar. 20, 2013.
International Peliminary Report on Patentability dated, Jul. 3, 2013.

*Primary Examiner* — T. Victor Oh
(74) *Attorney, Agent, or Firm* — Hansen IP Law PLLC

(57) ABSTRACT

A process for conditioning a high efficiency silver catalyst used to manufacture ethylene oxide from ethylene, oxygen, and at least one organic chloride is described. A non-reactive conditioning gas comprising at least one of ethylene, oxygen, and a ballast gas is introduced to the catalyst at a conditioning temperature ranging from 150° C. to 180° C. for a selected period of at least 4 hours.

15 Claims, 4 Drawing Sheets

PROCESS FOR CONDITIONING A HIGH EFFICIENCY ETHYLENE OXIDE CATALYST

TECHNICAL FIELD

This disclosure relates generally to processes for making ethylene oxide, and more specifically, to a method of conditioning a high efficiency ethylene oxide catalyst to improve its performance in the production of ethylene oxide.

BACKGROUND

Ethylene oxide has a multiplicity of utilities. Ethylene oxide, for example, is used to produce ethylene glycol, which is used as an automotive coolant, as antifreeze, and in preparing polyester fibers and resins, nonionic surfactants, glycol ethers, ethanolamines, and polyethylene polyether polyols.

The production of ethylene oxide via catalytic epoxidation of ethylene in the presence of oxygen using silver based catalysts is known. Conventional silver-based catalysts used in such processes typically provide a relatively lower efficiency or "selectivity" (i.e., a lower percentage of the reacted ethylene is converted to the ethylene oxide). In certain exemplary processes, when using conventional catalysts in the epoxidation of ethylene, the theoretically maximal efficiency towards ethylene oxide, expressed as a fraction of the ethylene converted, does not reach values above the 6/7 or 85.7 percent limit. Therefore, this limit had long been considered to be the theoretically maximal efficiency of this reaction, based on the stoichiometry of the following reaction equation:

cf. Kirk-Othmer's Encyclopedia of Chemical Technology, 4th ed., Vol. No. 9, 1994, p. 926.

Certain "high efficiency" or "high selectivity" modern silver-based catalysts are highly selective towards ethylene oxide production. For example, when using certain modern catalysts in the epoxidation of ethylene, the theoretically maximal efficiency towards ethylene oxide can reach values above the 6/7 or 85.7 percent limit referred to, for example 88 percent or 89 percent, or above. As used herein, the terms "high efficiency catalyst" and "high selectivity catalyst" refer to a catalyst that is capable of producing ethylene oxide from ethylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency at any point during its life, for example, under any set of reaction conditions as described in the Examples hereinafter, or by extrapolating lower efficiencies observed at two different oxygen conversions obtained by varying gas hourly space velocity to the limiting case of zero oxygen conversion, it is considered to be a high efficiency catalyst. Such highly efficient catalysts, which may comprise as their active components silver, rhenium, at least one further metal, and optionally, a rhenium co-promoter, are disclosed in EP0352850B1 and in several subsequent patent publications. "Promoters," sometimes referred to as "inhibitors" or "moderators," refer to materials that enhance the performance of the catalysts by either increasing the rate towards the desired formation of ethylene oxide and/or suppressing the rate towards the undesirable oxidation of ethylene or ethylene oxide to carbon dioxide and water. As used herein, the term "co-promoter" refers to a material that—when combined with a promoter—increases the promoting effect of the promoter.

"Promoters" can be materials that are introduced to catalysts during the preparation of the catalysts (solid phase promoters). In addition, "promoters" can also be gaseous materials that are introduced to the epoxidation reactor feed (gas phase promoters). In one example, an organic halide gas phase promoter may be added continuously to the epoxidation reactor feed to increase the catalyst efficiency. For silver-based ethylene epoxidation catalysts, both solid and gas phase promoters are typically required in any commercial processes.

Conventional catalysts have relatively flat efficiency curves with respect to the gas phase promoter concentration in the feed, i.e., the efficiency is almost invariant (i.e., the change in efficiency with respect to a change in gas phase promoter concentration in the feed is less than about 0.1%/ppm) over a wide range of promoter concentrations, and this invariance is substantially unaltered as reaction temperature is changed (i.e., the change in efficiency with respect to a change in reaction temperature is less than about 0.1%/° C.) during prolonged operation of the catalyst. However, conventional catalysts have nearly linear activity decline curves with respect to the gas phase promoter concentration in the feed, i.e., with increasing gas phase promoter concentration in the feed, temperature has to be increased or the ethylene oxide production rate will be reduced. Therefore, when using a conventional catalyst, for optimum efficiency, the gas phase promoter concentration in the feed can be chosen at a level at which the maximum efficiency can be maintained at relatively lower operating temperatures. Typically, the gas phase promoter concentration can remain substantially the same during the entire lifetime of a conventional catalyst. Alternatively, the reactor temperature may be adjusted to obtain a desired production rate without any substantial impact on efficiency due to non-optimal gas phase promoter concentrations.

By contrast, high efficiency catalysts tend to exhibit relatively steep efficiency curves as a function of gas phase promoter concentration as the concentration moves away from the value that provides the highest efficiency (i.e., the change in efficiency with respect to a change in gas phase promoter concentration is at least about 0.2%/ppm when operating away from the efficiency maximizing concentration). Thus, small changes in the promoter concentration can result in significant efficiency changes, and the efficiency exhibits a pronounced maximum, i.e., an optimum, at certain concentrations (or feed rates) of the gas phase promoter for a given reaction temperature and catalyst age. Moreover, the efficiency curves and the optimum gas phase promoter concentration tend to be strong functions of reactor temperature and are thus significantly affected if reactor temperature is varied, for example, to compensate for decreases in catalyst activity, (i.e., the change in efficiency with respect to a change in reactor temperature can be at least about 0.1%/° C. when operating away from the efficiency maximizing promoter concentrations for the selected temperatures). In addition, high efficiency catalysts have exhibited significant activity increases with increases in the gas phase promoter concentration in the feed, i.e., with increasing gas phase promoter concentration in the feed, temperature has to be decreased or the production rate will increase.

High-efficiency catalysts for producing ethylene oxide are frequently conditioned or activated prior to start-up to improve their activity and/or efficiency. Conditioning and activation processes typically involve flowing a non-reactive medium through the heated catalyst. Conditioning processes typically take place prior to the start of ethylene oxide production. Activation processes can take place both before and after starting ethylene oxide production. However, as used herein, the term "conditioning" refers to processes occurring either before or after start-up. The duration and conditions of the catalyst bed during the conditioning or activation period, such as feed gas composition, feed gas flow rate, space velocity, temperature, and pressure can influence the catalyst performance that is observed after stable operation is reached. Thus, a need has arisen for conditioning and activation processes that provide improved performance after start-up.

SUMMARY

A process for conditioning a high efficiency silver catalyst used to manufacture ethylene oxide by reacting ethylene, oxygen, and at least one organic chloride over the catalyst is provided. The conditioning process comprises the steps of introducing a feed gas to the high efficiency silver catalyst at one or more conditioning temperatures ranging from 150° C. to 180° C. for a selected period of time. The selected period of time is at least 4 hours, and the feed gas comprises at least one component selected from the group consisting of ethylene, oxygen, methane, and nitrogen. During the introducing step, the catalyst is not simultaneously exposed to both ethylene and oxygen, thereby ensuring that the reaction between ethylene and oxygen will not take place during the selected period of time. A process for manufacturing ethylene oxide by reacting ethylene, oxygen, and at least one organic chloride over a high-efficiency silver catalyst is also provided which comprises performing the foregoing conditioning process and introducing a second feed gas to the high efficiency silver catalyst, wherein the second feed gas comprises ethylene, oxygen, and the at least one organic chloride, and the ethylene and the oxygen react to form the ethylene oxide.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

DETAILED DESCRIPTION

Figure 1:
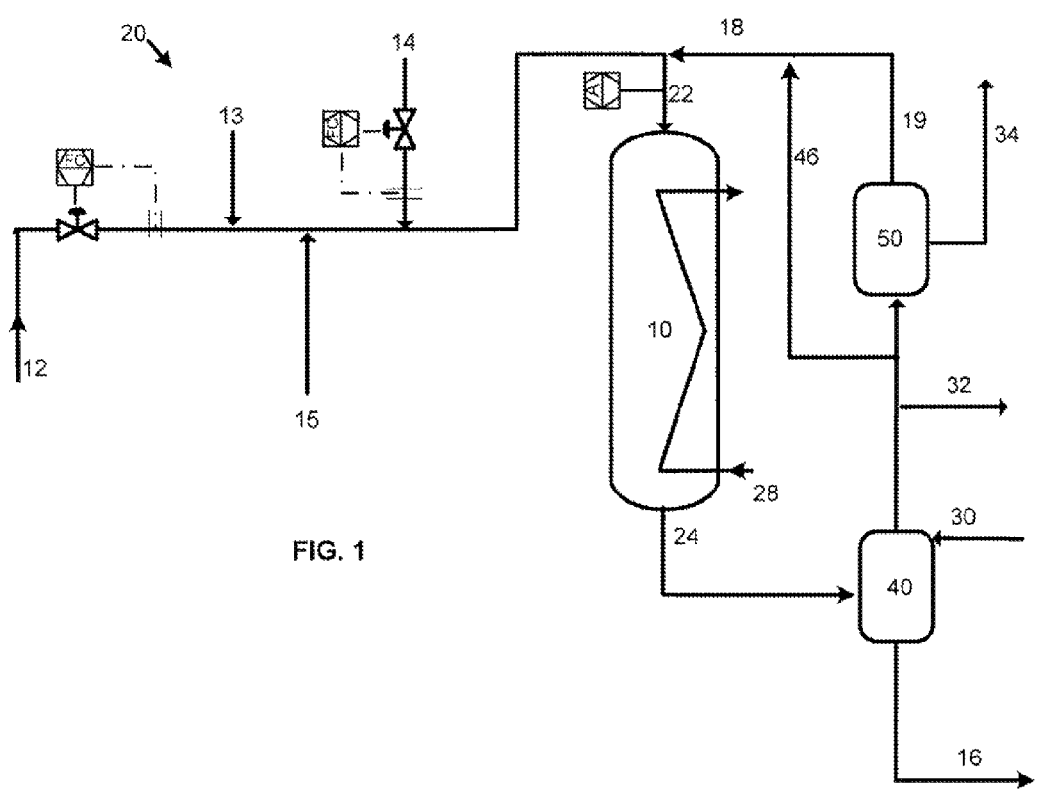
FIG. 1 is a process flow diagram depicting an embodiment of a process for making ethylene oxide by epoxidizing ethylene over a high efficiency catalyst.

The present disclosure provides a method for conditioning a high-efficiency silver catalyst used to manufacture ethylene oxide by reacting a feed gas comprising ethylene, oxygen, and at least one organic chloride over the catalyst. As explained in detail below, it has been found that the introduction of a non-reactive conditioning medium comprising selected feed gas components to such a catalyst at conditioning temperatures ranging from 150° C. to 180° C. for a selected period of time of at least four (4) hours, preferably at least twelve (12) hours, and more preferably at least sixteen (16) hours, provides unexpected improvements in catalyst performance following start-up. It has also been found that the catalyst conditioning methods described herein achieve such benefits with fresh catalysts, aged catalysts, and when re-starting a high-efficiency silver catalyst following an unexpected shutdown such as resulting from the occurrence of a reactor trip condition.

In order to facilitate an understanding of the present disclosure, it is useful to define certain terms relating to catalyst and process performance. The "activity" of a catalyst in a fixed bed reactor is generally defined as the reaction rate towards the desired product per unit of catalyst volume in the reactor. The activity relates to both the total number of available active sites and the reaction rate of each site. The number of active sites can be reduced in several ways. For example, they can be reduced by coalescence of the silver particles, which reduces the surface area of the silver available for reaction. They can also be reduced by poisoning, for example by reaction with trace sulfur compounds in the reactor feed. The number of active sites can also be reduced by reaction with normal process constituents, such as by reaction with chloride compounds in the process stream to form silver chloride compounds, which are inactive towards the epoxidation reaction. The activity will also decline if the reaction rate goes down for at least some of the active sites (e.g., due to localized poisoning) independent of the total number of active sites. To compensate for the activity decline in order to maintain a given production rate, certain reaction conditions have to be changed to increase the overall production rate of the available active sites. For instance, reaction temperature is often raised to provide more energy to the active sites for this purpose. "Activity" can be quantified in a number of ways, one being the mole percent of ethylene oxide contained in the outlet stream of the reactor relative to that in the inlet stream (the mole percent of ethylene oxide in the inlet stream typically, but not necessarily, approaches zero percent) while the reactor temperature is maintained substantially constant; and another being the temperature required to maintain a given rate of ethylene oxide production. In many instances, activity is measured over a period of time in terms of the mole percent of ethylene oxide produced at a specified constant temperature. Alternatively, activity may be measured as a function of the temperature required to sustain production of a specified constant mole percent of ethylene oxide, given other conditions such as pressure and total moles in the feed.

The "efficiency" of the epoxidation, which is synonymous with "selectivity," refers to the relative amount (as a fraction or in percent) of converted or reacted olefin that forms a particular product. For example, the "efficiency to ethylene oxide" refers to the percentage on a molar basis of converted or reacted ethylene that forms ethylene oxide. The "yield" of ethylene oxide refers to the net number of moles of ethylene oxide produced by the process divided by the net number of moles of ethylene fed to the process for any given time period.

The term "ethylene oxide production parameter" is used herein to describe a variable that relates to the extent to which ethylene oxide is produced. Examples of ethylene oxide production parameters include, without limitation, ethylene oxide concentration, ethylene oxide yield, ethylene oxide production rate, ethylene oxide production rate/catalyst volume, ethylene conversion, and oxygen conversion. Thus, the ethylene oxide concentration relates to the ethylene oxide production rate because the production rate may be obtained by multiplying the ethylene oxide concentration and the product flow rate. Depending on the configuration of the process, an ethylene oxide production rate may be determined at the reactor outlet, downstream of a reactor outlet recycle stream, or downstream of separation processes (e.g., scrubbers) used to extract the ethylene oxide product. As used herein, the term "reaction product" includes unreacted feed components as well as those that are generated as a result of a chemical reaction. In the example of ethylene oxide processes, the "reaction product" would include ethylene oxide, and if present, any by-products (such as carbon dioxide and water) or unreacted feed components (such as ethylene, oxygen, and/or chlorides). The ethylene oxide production rate/catalyst volume may be determined by dividing the production rate by the volume of the catalyst bed. The oxygen and ethylene conversions are related to the production of the ethylene oxide by the efficiency.

As is known in the art, as a reaction is carried out over a catalyst over a period of time, the catalyst eventually begins to "age" and lose activity, which typically means that the number of active sites available for catalyzing the desired reaction are reduced. One measure of catalyst age is the total production of ethylene oxide on a mass basis (e.g., using metric kilotons "kt") divided by the catalyst-packed reactor volume (e.g., in cubic meters) in reactor 10. Another measure of catalyst age is the total production of ethylene oxide on a molar basis divided by the catalyst-packed reactor volume. As used herein, the term "fresh catalyst" includes catalysts that have not yet been exposed to a reactive epoxidation feed gas. However, the term also includes and more broadly refers to catalysts that have not aged beyond a certain threshold. As used herein, the term "fresh catalyst" means a catalyst that has not aged or which has aged by an amount no greater than 0.2 kt ethylene oxide/cubic meter of catalyst.

FIG. 1 is a simplified schematic that illustrates a process 20 for making ethylene oxide. Process 20 includes a reactor 10 comprising a tubular vessel with a catalyst bed disposed in it. Olefin (i.e., ethylene) feed stream 12 (which may also include saturated hydrocarbons, such as ethane, as an impurity) is combined with ballast gas 13, oxygen feed 15 and gas phase promoter feed 14 to define reactor feed gas inlet stream 22 proximate the reactor inlet. Reactor product stream 24 includes the ethylene oxide ("EO") product, plus side products (e.g., $CO_2$, $H_2O$, and small amounts of saturated hydrocarbons), unreacted ethylene, oxygen, and inerts. Water stream 30 is added to ethylene oxide absorber 40 to absorb ethylene oxide product from reactor product stream 24. Net product stream 16 comprises water and ethylene oxide, and the ethylene oxide is subsequently separated from the water.

If desired, recycle stream 18 may also be provided to recycle unreacted ethylene and oxygen. One example of a suitable recycle system is depicted in FIG. 1. As shown in the figure, ethylene oxide absorber 40 produces an overhead gas stream comprising unreacted ethylene and oxygen, saturated hydrocarbon impurities or byproducts, and carbon dioxide. Carbon dioxide is removed in an optional $CO_2$ removal unit 50 (e.g., a $CO_2$ scrubber) and exits optional $CO_2$ removal unit 50 in carbon dioxide stream 34. The overhead stream 19 from unit 50 is combined with optional $CO_2$ removal unit 50 bypass stream 46 to define recycle stream 18. Recycle stream 18 is combined with ethylene feed 12, ballast gas 13, oxygen feed 15, and gas phase promoter feed 14 to define reactor feed stream 22. Purge line 32 is also provided to provide for the removal of saturated hydrocarbon impurities (e.g., ethane), inerts (such as argon), and/or byproducts (as well as carbon dioxide) to prevent their accumulation in reactor feed 22.

Oxygen feed 15 may comprise substantially pure oxygen or air. Ballast gases or diluents 13 such as nitrogen or methane may also be included to maintain the oxygen concentration below the maximum level allowed by flammability considerations. The concentration of oxygen in reactor feed stream 22 may vary over a wide range, and in practice, flammability is generally the limiting factor for oxygen concentration. Generally, at steady-state the oxygen concentration in reactor feed 22 will be at least one (1) mole percent and preferably at least two (2) mole percent. The oxygen concentration will generally be no more than fifteen (15) mole percent and preferably no more than twelve (12) mole percent. The ballast gas 13 (e.g., nitrogen or methane) is generally from 50 mole percent to 80 mole percent of the total composition of reactor feed stream 22. One reason methane ballast gas is preferred over nitrogen is because, due to its higher heat capacity, methane facilitates the use of higher oxygen concentrations in the cycle, and therefore, improves both activity and efficiency.

The steady-state concentration of ethylene in reactor feed stream 22 may vary over a wide range. However, it is preferably at least eighteen (18) mole percent and more preferably at least twenty (20) mole percent. The concentration of ethylene in reactor feed stream 22 is preferably no greater than 50 mole percent, and more preferably is no greater than 40 mole percent.

When present, the carbon dioxide concentration in reactor feed stream 22 has a large adverse effect on the efficiency, activity and/or stability of catalysts used in reactor 10. Carbon dioxide is produced as a reaction by-product and may also be introduced with other inlet reaction gases as an impurity. In commercial ethylene epoxidation processes, at least part of the carbon dioxide is removed continuously in order to control its concentration to an acceptable level in the cycle. For high efficiency catalysts, the carbon dioxide concentration in reactor feed 22 is generally no more than 5 mole percent, preferably no more than 3 mole percent, and even more preferably no more than 2 mole percent of the total composition of reactor feed 22. Water may also be present in the feed gases, and may be present in concentrations that are preferably from 0 to no more than two (2) mole percent.

The gas phase promoter 14 is generally a compound that enhances the efficiency and/or activity of process 20 for producing ethylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred. Using chlorohydrocarbons gas phase promoters as an example, it is believed that the ability of the promoter to enhance the performance (e.g., efficiency and/or activity) of process 20 depends on the extent to which the gas phase promoter chlorinates the surface of the catalyst in reactor 10, for example, by depositing particular chlorine species such as atomic chlorine or chloride ions on the catalyst. However, hydrocarbons lacking chlorine atoms are believed to strip chlorides from the catalyst, and therefore, detract from the overall performance enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communications*, Vol. 82 (1989) at 229-232 and Berty, "Ethylene Oxide Synthesis," *Applied Industrial Catalysis*, Vol. I (1983) at 207-238. Paraffinic compounds, such as ethane or propane, are believed to be especially effective at stripping chlorides from the catalyst. However, olefins such as ethylene and propylene, are also believed to act to strip chlorides from the catalyst. Some of these hydrocarbons may also be introduced as impurities in the ethylene feed 12 or may be present for other reasons (such as the use of recycle stream 18). Typically, the preferred concentration of ethane in the reactor feed 22 is from 0 to 2 mole percent. Given the competing effects of the gas phase promoter and the Cl-removing hydrocarbons in reactor feed stream 22, it is convenient to define an "overall catalyst chloriding effectiveness value" that represents the net effect of gas phase species in chloriding the catalyst. In the case of organic chloride gas-phase promoters, the overall catalyst chloriding effectiveness can be defined as the dimensionless quantity Z* and represented by the following formula:

$$Z^* = \frac{\text{ethyl chloride equivalent }(ppmv)}{\text{ethane equivalent (mole percent)}} \quad (1)$$

wherein the ethyl chloride equivalent is the concentration in ppmv of ethyl chloride that provides substantially the same catalyst chloriding effectiveness of the organic chlorides present in reactor feed stream 22 at the concentrations of the organic chlorides in feed stream 22; and the ethane equivalent is the concentration of ethane in mole percent that provides substantially the same catalyst dechloriding effectiveness of the non-chloride containing hydrocarbons in the reactor feed stream 22 at the concentrations of the non-chloride containing hydrocarbons in the reactor feed stream 22.

If ethyl chloride is the only gaseous chloride-containing promoter present in reactor feed stream 22, the ethyl chloride equivalent (i.e., the numerator in equation (1)) is the ethyl chloride concentration in ppmv. If other chlorine-containing promoters (specifically vinyl chloride, methyl chloride or ethylene dichloride) are used alone or in conjunction with ethyl chloride, the ethyl chloride equivalent is the concentration of ethyl chloride in ppmv plus the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance (and hence the same value of Z*) provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed of 1 ppmv ethylene dichloride and 1 ppmv ethyl chloride, the ethyl chloride equivalent in the numerator of Z* would then be 3 ppmv. As a further example, it has been found that for certain catalysts methyl chloride has 10 times less the chloriding effectiveness of ethyl chloride (i.e. 10 ppmv methyl chloride is required to realize effectiveness in terms of catalyst performance equivalent to that of 1 ppmv ethyl chloride). Therefore, for such catalysts the ethyl chloride equivalent for a given concentration of methyl chloride in ppmv is 0.1× (methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppm is 1.0×(vinyl chloride concentration in ppmv). When more than two chlorine-containing promoters are present in reactor feed stream 22, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of Z* would be 2*1+1+1*1=4 ppmv.

The ethane equivalent (i.e., the denominator in equation (1)) is the concentration of ethane in mole percent in reactor feed stream 22 plus the concentration of the other hydrocarbons effective in removing chloride from the catalysts, corrected for their effectiveness for dechlorination relative to ethane. The relative effectiveness of ethylene compared to ethane can be measured experimentally by determining the inlet ethyl chloride equivalent concentration that provides the same level of catalyst performance (and hence the same value of Z*) for a feed comprising both ethylene and ethane as compared to the same feed with the same ethylene concentration but a specific ethyl chloride equivalent concentration and no ethane. As a way of further illustration, if with a feed composition comprising an ethylene concentration of 30.0 mole percent and an ethane concentration of 0.30 mole percent, a level of 6.0 ppm ethyl chloride equivalents is found to provide the same level of catalyst performance as 3.0 ppm ethyl chloride equivalents with a similar feed composition but lacking ethane, then to obtain the same value of Z* in both cases the ethane equivalent for 30.0 mole percent ethylene would be 0.30 mole percent. For an inlet reactor feed 22 having 30.0 mole percent ethylene and 0.3 mole percent ethane, the ethane equivalent will then be 0.6 mole percent. As another illustration, it has been found that for certain catalysts methane has 500 times less the dechloriding effectiveness of ethane. Thus, for such catalysts the ethane equivalent for methane is 0.002×(methane concentration in mol %). For a hypothetical inlet reactor feed 22 having 30.0 mole percent ethylene and 0.1 mole percent ethane, the ethane equivalent then will be 0.4 mole percent. For an inlet reactor feed 22 having 30.0 mole percent ethylene, 50 mole percent methane, and 0.1 mole percent ethane, the ethane equivalent then will be 0.5 mole percent. The relative effectiveness of hydrocarbons other than ethane and ethylene can be measured experimentally by determining the inlet ethyl chloride equivalent concentrations required to achieve the same catalyst performance (and hence the same value of Z*) for a feed comprising the hydrocarbon of interest at its concentration in the feed at two different concentrations of ethane in the feed. If a hydrocarbon compound is found to have a very small dechloriding effect and is also present in low concentrations, then its contribution to the ethane equivalent concentration in the Z* calculation may be negligible.

Thus, given the foregoing relationships, in the case where reactor feed stream 22 includes ethylene, ethyl chloride, ethylene dichloride, vinyl chloride, and ethane, the overall catalyst chloriding effectiveness value of process 20 can be defined as follows:

$$Z^* = \frac{(ECL + 2^*EDC + VCL)}{(C_2H_6 + 0.01^*C_2H_4)} \quad (2)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C$=CH—Cl), respectively, in reactor feed stream 22. $C_2H_6$ and $C_2H_4$ are the concentrations in mole percent of ethane and ethylene, respectively, in reactor feed stream 22. It is important that the relative effectiveness of the gaseous chlorine-containing promoter(s) and the hydrocarbon dechlorinating species also be measured under the reaction conditions which are being used in the process and confirmed to be appropriate over the ranges expected for such conditions. $Z^*$ will preferably be maintained at a level that is no greater than 20 and which is most preferably no greater than 15. $Z^*$ is preferably at least 1.

Although the gaseous chlorine-containing promoter may be supplied as a single species, upon contact with the catalyst, other species may be formed leading to a mixture in the gas phase. Consequently, if the reaction gases are recycled such as via recycle stream 18, a mixture of species will be found in the inlet of the reactor. In particular, the recycled reaction gases at the inlet may contain ethyl chloride, vinyl chloride, ethylene dichloride and methyl chloride, even though only ethyl chloride or ethylene dichloride is supplied to the system. The concentrations, if present, of at least ethyl chloride, vinyl chloride, and ethylene dichloride must be considered in calculating the ethyl chloride equivalent and $Z^*$.

The order in which the feed gases (ethylene and oxygen and ballast gas) and gas phase promoter are mixed together is not critical, and they may be mixed simultaneously or sequentially. The order of mixing of the gaseous components of the process may be chosen for convenience and/or for safety reasons. For example, oxygen is generally added after ethylene and the ballast gas for reasons of safety.

In the embodiment of FIG. 1, Reactor 10 is a fixed bed tubular reactor. However, any suitable reactor may be used, for example, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics. The ethylene epoxidation reaction is exothermic. Thus, a coolant system 28 (e.g., a cooling jacket or a hydraulic circuit with a coolant fluid such as a heat transfer fluid or boiling water) is provided to regulate the temperature of reactor 10. As will be discussed further below, in certain preferred embodiments, the coolant system 28 may also function as a heating system by adjusting the temperature of the heat transfer medium when performing the catalyst conditioning methods described herein. The heat transfer fluid can be any of several well-known heat transfer fluids, such as tetralin (1,2, 3,4-Tetrahydronaphthalene). In reactors cooled with boiling water, the coolant is introduced to the cooling side of the reactor, most commonly the shell side of the reactor, as liquid water. As it flows through the cooling side, the water removes heat from the process side, and some of the water is vaporized to steam. The coolant exits the cooling side of the reactor as a mixture of water and steam. The steam exiting the reactor shell is removed and/or condensed by removing heat from it, and the condensed water is recycled back to the inlet of the coolant side. The temperature of the coolant in the reactor shell is determined by the boiling point of the water, which in turn is determined by the pressure under which it operates. The shell side pressure is controlled by means of a vent valve which vents off some steam. Typically, a closed-loop controller is used to regulate the coolant temperature by automatically adjusting the vent valve to maintain the pressure necessary to maintain the desired temperature.

It should be noted that the terms "reactor temperature," "reaction temperature," "epoxidation temperature" or "epoxidation reaction temperature" refer to any selected temperature(s) that are directly or indirectly indicative of the catalyst bed temperature. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor coolant inlet or outlet temperature. The epoxidation reaction is carried out at a temperature that is preferably at least 200° C., more preferably at least 210° C., and most preferably at least 220° C. Reactor temperatures of no more than 300° C. are preferred, and reactor temperatures of no more than 290° C. are more preferred. Reactor temperatures of no more than 280° C. are most preferred. The reactor pressure is selected based on the desired mass velocity and productivity and ranges generally from 5 atm (506 kPa) to 30 atm (3.0 MPa). The gas hourly space velocity (GHSV) is preferably greater than 3000 $h^{-1}$, more preferably greater than 4,000 $hr^{-1}$, and most preferably greater than 5,000 $h^{-1}$.

Reactor 10 includes a high efficiency, silver catalyst. Generally, the highly efficient silver based catalyst is a supported catalyst. The support (also known as a "carrier") may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina. In one exemplary embodiment, silver is deposited on the catalyst carrier as are one or more solid promoters, which are discussed further below.

There are many well-known methods of preparing supports suitable for use in ethylene oxide catalysts. Some of such methods are described in, for example, U.S. Pat. Nos. 4,379, 134; 4,806,518; 5,063,195; 5,384,302, U.S. Patent Application 20030162655 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives. Another method for preparing a carrier having particularly suitable properties for ethylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina carrier.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the carrier may comprise compounds which have been known for improving catalyst performance, for example, rhenium, (such as rhenates) and molybdenum.

The alpha-alumina carrier prepared as described hereinabove preferably has a specific surface area of at least 0.5 $m^2/g$, and more preferably, at least 0.7 $m^2/g$. The surface area is typically less than 10 $m^2/g$, and preferably, less than 5 $m^2/g$. The alpha-alumina carrier preferably has a pore volume of at least 0.3 $cm^3/g$, and more preferably, from 0.4 $cm^3/g$ to 1.0 $cm^3/g$ and a median pore diameter from 1 to 50 microns. A variety of carrier morphologies may be used, including pills, cylinders, cylinders with one or more longitudinal axial openings, chunks, tablets, pieces, pellets, rings, spheres, wagon wheels, saddle rings and toroids having star shaped inner and/or outer surfaces. In a preferred embodiment, the high-purity alpha-alumina preferably includes particles many of which have at least one substantially flat major surface, and having a lamellate or platelet morphology. In a more preferred embodiment the particles approximate the shape of a hexagonal plate (some particles having two or more flat surfaces), at least 50 percent of which (by number) have a major dimension of less than 50 microns. In a preferred embodiment, the alpha-alumina carrier comprises zirconium silicate (zircon), present substantially as zirconium silicate in the finished carrier.

Catalysts of this invention for the production of ethylene oxide, may be prepared with the aforementioned carriers by impregnating the carrier with a solution of one or more silver compounds, depositing the silver throughout the pores of the carrier and reducing the silver compound as is well known in the art. See for example, Liu, et al., U.S. Pat. No. 6,511,938 and Thorsteinson et al., U.S. Pat. No. 5,187,140.

Generally, the carrier is impregnated with a catalytic amount of silver, which is any amount of silver capable of catalyzing the direct oxidation of ethylene with oxygen or an oxygen-containing gas to ethylene oxide. In making such a catalyst, the carrier is typically impregnated (one or more times) with one or more silver compound solutions sufficient to allow the silver to be supported on the carrier in an amount between 5 percent and less than 70 percent, and preferably greater than 30 and less than 50 percent by weight, based on the weight of the catalyst.

As is known to those skilled in the art, there are a variety of known promoters, that is, materials which, when present in combination with particular catalytic materials, for example, silver, benefit one or more aspect of catalyst performance or otherwise act to promote the catalyst's ability to make a desired product, for example ethylene oxide or propylene oxide. There are at least two types of promoters—solid promoters and gaseous promoters. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261. The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counterion added during the preparation of the catalyst. The catalyst prepared on the carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. Note that references to the Periodic Table herein shall be to that as published by the Chemical Rubber Company, Cleveland, Ohio, in CRC Handbook of Chemistry and Physics, 46th Edition, inside back cover.

The concentration of alkali metal (based on the weight of cation, for example cesium) promoters in the finished catalyst may vary from 0.0005 to 1.0 wt. %, preferably from 0.005 to 0.5 wt. %. The preferred amount of cation promoter deposited on or present on the surface of the carrier or catalyst generally lies between 10 and 5000, preferably 15 and 3000, and more preferably between 20 and 2500 ppm by weight of cation calculated on the total carrier material. Cation promoter amounts between 50 and 2000 ppm by weight of the total carrier material are frequently most preferable. When the alkali metal cesium cation is used in mixture with other cations, the ratio of cesium to any other alkali metal and alkaline earth metal cation(s), if used, to achieve desired performance is not narrow and may vary over a wide range. The weight ratio of cesium to the other cation promoters may vary from 0.0001:1 to 10,000:1, preferably from 0.001:1 to 1,000:1.

Anion promoters or modifiers which may be employed with the present invention are those known to those of skill in the art and examples include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications. The invention is not intended to be limited by the exact species that may ultimately exist on the catalyst during use.

With certain highly efficient catalysts, the most preferred promoter comprises rhenium, which can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $[ReO_4]^-$. Similar chemistries can be exhibited by other metals such as molybdenum and tungsten.

The amount of anion promoter may vary widely, for example, from 0.0005 to 2 wt. %, preferably from 0.001 to 0.5 wt. % based on the total weight of the catalyst. When used, the rhenium component is often provided in an amount of at least 1, say, at least 5, for example, 10 to 2000, often between 20 and 1000, ppmw calculated as the weight of rhenium based on the total weight of the catalyst.

It is desirable that the silver and one or more solid promoters be relatively uniformly dispersed on the carrier. A preferred procedure for depositing silver catalytic material and one or more promoters comprises: (1) impregnating a carrier according to the present invention with a solution comprising a solvent or solubilizing agent, silver complex and one or more promoters, and (2) thereafter treating the impregnated carrier to convert the silver compound and effect deposition of silver and the promoter (s) onto the exterior and interior pore surfaces of the carrier. Silver and promoter depositions are generally accomplished by heating the solution containing carrier at elevated temperatures to evaporate the liquid within the carrier and effect deposition of the silver and promoters onto the interior and exterior carrier surfaces. The temperature of the heating step is high enough to reduce any silver compounds to metallic silver. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

Well known methods can be employed to analyze for the amounts of silver and solid promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

Figure 2:
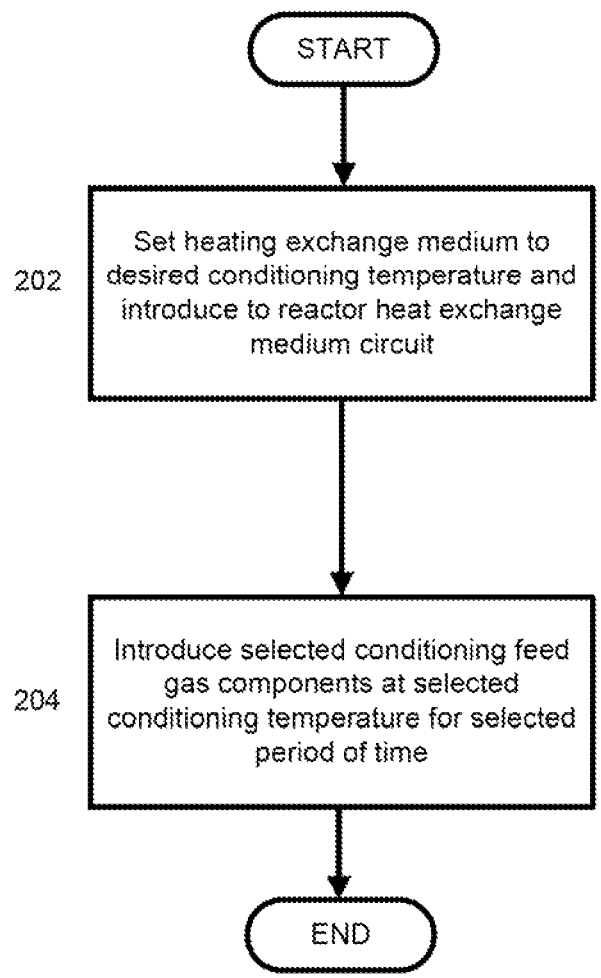
FIG. 2 is a flow chart depicting an embodiment of a method of conditioning a high-efficiency silver catalyst used in the process of FIG. 1.

Referring to FIG. 2, a method of conditioning a high-efficiency silver catalyst used to epoxidize ethylene is depicted. In step 202 of FIG. 2, a heat transfer medium is supplied to the coolant circuit of reactor 10 to adjust the catalyst temperature to a conditioning temperature. The temperature of the heat transfer medium is set higher than the temperature of the catalyst in the reactor, thereby causing the catalyst temperature to increase. During an epoxidation reaction, the heat transfer medium absorbs heat generated from the exothermic epoxidation reaction. However, in step 202, the heat transfer medium transfers heat to the catalyst, thereby raising the catalyst temperature. It should be noted that the term "conditioning temperature" refers to any selected temperature(s) that are directly or indirectly indicative of the catalyst bed temperature during a catalyst conditioning process. In certain embodiments, the conditioning temperature may be a catalyst bed temperature at a specific location in the catalyst bed. In other embodiments, the conditioning temperature may be a numerical average of several catalyst bed temperature measurements made along one or more catalyst bed dimensions (e.g., along the length). In additional embodiments, the conditioning temperature may be the reactor coolant inlet or outlet temperature. In other embodiments, the conditioning temperature may be the reactor outlet gas temperature. The conditioning temperature selected in step 202 ranges from greater than the non-reactive feed gas dew point (i.e., the dew point of the conditioning gas used in step 204) to 180° C. In one embodiment, the lower limit of the conditioning temperature is 150° C.

In step 204, the non-reactive conditioning feed gas is introduced to reactor 10 for the selected conditioning period, which is generally at least 4 hours, preferably at least 12 hours, and more preferably at least 16 hours. At the same time, the selected conditioning period is generally no greater than 200 hours, more preferably no greater than 180 hours, and still more preferably no greater than 140 hours. In certain embodiments, the conditioning medium is substantially all ballast gas, e.g., either nitrogen or methane, in which case both ethylene and oxygen are supplied to begin start-up. In other embodiments, the conditioning medium is substantially all ethylene or a mixture of ethylene and ballast gas, in which case oxygen and ballast gas or oxygen, respectively, are supplied to begin start-up. Oxygen and/or combinations of oxygen and nitrogen may also be used as a conditioning medium, in which case ethylene and nitrogen or ethylene, respectively, are supplied to begin start-up. In examples wherein mixtures of ethylene and other components are used as the conditioning medium, the amount of ethylene present in the feed gas (on a molar basis) is preferably at least 5 percent, more preferably at least 10 percent, and even more preferably at least 20 percent of the total feed gas.

During the selected conditioning period, the temperature and/or flow rate of the heat transfer medium are preferably adjusted as necessary to maintain the conditioning temperature between 150° C. and 180° C. throughout the selected conditioning period. The conditioning temperature may be maintained at a single temperature or at a plurality of temperatures between 150° C. and 180° C. In certain embodiments, it is preferable to progressively increase the conditioning temperature toward an epoxidation temperature throughout all or part of the conditioning process such as by using a ramp function, a series of steps, or by non-linearly increasing the conditioning temperature to a maximum that is no greater than 180° C. The conditioning temperature may be manipulated manually or automatically with the coolant (heating) circuit temperature controller (not shown in the figures).

The conditioning process of FIG. 2 may be used in a process for manufacturing ethylene oxide by reacting ethylene, oxygen, and at least one organic chloride over a high efficiency silver catalyst to yield a product comprising ethylene oxide. In such manufacturing processes, following the performance of the conditioning process of FIG. 2 with a first feed gas, reactor 10 may be started-up by setting the heat exchange medium to a desired start-up epoxidation temperature and adjusting the composition of the feed gas to provide a second, reactive (start-up) feed gas at reactor inlet 22. The second reactive (start-up) feed gas 22 is then fed to reactor 10. The second reactive (start-up) feed gas comprises ethylene in an amount (on a molar basis) that is generally at least 5 percent, more preferably at least 10 percent, still more preferably at least 15 percent, and even more preferably at least 20 percent of the total feed gas. At the same time, the amount (on a molar basis) of ethylene present in the second reactive (start-up) feed gas is preferably no greater than 40 percent and more preferably no greater than 35 percent of the total feed gas.

During the start-up phase, the second reactive feed gas composition and/or other process variables are adjusted to achieve a desired value of an ethylene oxide production parameter as described previously. The manipulated process variables may include, without limitation, at least one of reaction temperature, overall chloriding effectiveness, feed gas ethylene concentration, feed gas oxygen concentration, gas hourly space velocity, and reactor pressure. In certain preferred implementations, the process variables may be manipulated to maintain the selected ethylene oxide production parameter at an optimum value. For example, the reactor temperature and overall chloriding effectiveness may be adjusted to achieve the maximum attainable efficiency at the selected value of the ethylene oxide production parameter and at a fixed process condition, such as a process condition at which one or more of ethylene concentration, oxygen concentration, reactor pressure, and gas hourly space velocity is held constant. In another example, the overall chloriding effectiveness may be adjusted to achieve the maximum attainable efficiency at the selected reaction temperature regardless of the value of an ethylene oxide production parameter. The feed gas composition at steady-state may be referred to herein as a "third feed gas composition" to distinguish the steady-state condition of the process 20 from the start-up condition and the conditioning process, even though the feed gas composition may not change between start-up and steady state.

In certain embodiments, the oxygen concentration in the second reactive (start-up) feed gas is typically adjusted following start-up to reach a maximum allowable level dictated by feed gas flammability considerations. In accordance with such embodiments, the amount of oxygen (on a molar basis) is preferably at least one (1) percent, more preferably at least two (2) percent, and still more preferably at least four (4) percent of the total feed gas. The amount of oxygen (on a molar basis) is preferably no greater than 15 percent, more preferably no greater than 10 percent, and still more preferably no greater than eight (8) percent of the total feed gas. In other embodiments, the oxygen concentration may not be adjusted to the maximum allowable level, in particular if a lower ethylene oxide production rate is desired or if the reaction temperature is sufficiently low that maximum oxygen operation would preclude the attainment of an optimum efficiency to the ethylene oxide.

In the start-up phase, the epoxidation reaction will begin producing heat that is transferred to the heat transfer medium (e.g., boiling water) in the cooling circuit of reactor 10. In certain preferred embodiments, the flow rate and/or temperature of the heat transfer medium is adjusted to maintain a start-up epoxidation temperature of at least 200° C., preferably at least 210° C., more preferably at least 220° C. The start-up epoxidation temperature is preferably no greater than 300° C., more preferably no greater than 290° C. and still more preferably no greater than 280° C. In one exemplary embodiment, the foregoing epoxidation temperature ranges are reactor coolant inlet temperature ranges.

In certain embodiments of the conditioning processes described herein, it is preferable to start-up the epoxidation process with first (initial) respective values of the overall catalyst chloriding effectiveness and reaction temperature prior to the detection of epoxidation and then adjust the start-up conditions to second respective values of the overall catalyst chloriding effectiveness and reaction temperature once epoxidation is detected. In accordance with other embodiments, once epoxidation is detected, the reaction temperature and overall chloriding effectiveness are maintained within certain preferred ranges for a period of time that is from one (1) hour to six (6) hours, and more preferably from two (2) hours to (4) hours.

In accordance with one example, when a reactive mixture of ethylene, oxygen, and organic chloride promoter is first introduced to the high-efficiency catalyst, the reactor temperature is maintained between 215° C. and 223° C., and the overall chloriding effectiveness is preferably maintained at a $Z^*$ value greater than 2.0. Once epoxidation is detected, $Z^*$ is preferably decreased to a value of at least 2.0, and the reaction temperature is preferably increased to a value of from 223° C. to 230° C. for a period that is from one (1) hour to six (6) hours and more preferably from two (2) hours to four (4) hours. Once this initial start-up phase is complete, the process may be adjusted to an optimum condition in accordance with desired targets.

It should be noted that in certain situations, the use of the foregoing temperature and $Z^*$ values will result in a level of ethylene oxide production that is greater than desired. In such instances, it is preferable to reduce the concentration of oxygen in the feed gas while maintaining the foregoing temperature and $Z^*$ values to attain the desired ethylene oxide production level. It is believed that this method will better ensure that the high-efficiency catalyst attains and maintains high-efficiency operation than if temperature were reduced to effect the desired decrease in ethylene oxide production.

The conditioning process of FIG. 2 may be used on a fresh catalyst or on an aged catalyst. If used on an aged catalyst, the catalyst age is preferably no greater than 1.1 kt ethylene oxide/$m^3$ catalyst, even more preferably no greater than 0.9 kt ethylene oxide/$m^3$ catalyst, and still more preferably no greater than 0.8 kt ethylene oxide/$m^3$ catalyst. At steady-state, the selected ethylene oxide production parameter will generally fluctuate by no more than 5%, preferably no more than 4%, more preferably no more than 3% and still more preferably no more than 2% from the target value of the selected ethylene oxide production parameter.

In certain preferred embodiments, process 20 is started-up immediately following the completion of the catalyst conditioning method. However, this is not necessary, and the conditioning methods described herein may be performed prior to taking a shutdown of the reaction system and then subsequently starting it up again. In one example, wherein the conditioning methods are used prior to starting up a new catalyst in reactor 10, the catalyst is first loaded into the reactor and purged with an inert medium to remove residual air before beginning the conditioning method. Of course, when the conditioning methods are used following a reactor shutdown, the catalyst loading step will not necessarily be required (e.g., if reactor 10 is not taken out of service). Because air will typically enter the catalyst bed during the loading process, purging is carried out by introducing a non-reactive medium (e.g., nitrogen or methane) through the catalyst bed to remove any residual air. During the purge process, the temperature of the purge medium is not critical. However, reactor 10 is preferably heated to a temperature in excess of the atmospheric dew point to prevent the condensation of any water comprising part of the residual air in the catalyst bed.

The catalyst conditioning methods described herein may also be advantageously used to improve reactor performance following an unplanned shutdown or reactor trip. As used herein, the terms "shutdown" or "reactor shutdown" refer to a planned or unplanned event in which process 20 ceases to produce ethylene oxide and most typically involves a cessation of oxygen feed to reactor 10. In such cases, process 20 is operated with a first (reactive) epoxidation feed gas at a desired ethylene oxide production parameter value, preferably at steady-state, prior to the occurrence of a reactor trip condition. Following the reactor trip condition, the supply of reactive feed gas to reactor 10 is stopped. As used herein, a "reactor trip condition" is a condition that necessitates the manual or automatic shutdown of reactor 10. Non-limiting examples of reactor trip conditions include loss of coolant flow to the reactor coolant circuit, loss of power or other utilities, loss of carbon dioxide removal capability, downstream disturbances (e.g., in a downstream alkylene glycol unit fed by process 20), a recycle compressor failure, a loss of ethylene feed flow, a loss of oxygen feed flow, and a loss of ballast gas flow. After the supply of a reactive feed gas to reactor 10 is discontinued, the conditioning method—for example, the conditioning method of FIG. 2—is carried out with a second (non-reactive) conditioning feed gas 22. The heat exchange medium is then adjusted to its desired epoxidation temperature, followed by the introduction of a third (reactive) epoxidation start-up feed gas 22 to reactor 10. The third feed gas composition and/or other process variables are adjusted to achieve a desired steady-state value of an ethylene oxide production parameter as described previously.

It has been found that the use of the catalyst conditioning methods described herein in conjunction with re-starting a reactor following an unplanned shutdown or reactor trip yields a quicker attainment of a target ethylene oxide production parameter than would otherwise be possible.

The following examples demonstrate the improved epoxidation performance resulting from the use of the catalyst conditioning methods described herein.

EXAMPLE I

A continuously stirred tank reactor ("CSTR") is loaded with whole pills of a high-efficiency ethylene oxide catalyst containing a promoting amount of rhenium. The catalysts are conditioned by introducing a conditioning medium comprising ethylene, ballast gas, or other feed components at different conditioning temperatures (as indicated by the CSTR outlet temperature) for a conditioning period of 40 hours prior to an initial start-up or re-start of the reactor. In the tables below, the references to ethylene conditioning involve conditioning feed gas mixtures of ethylene and nitrogen in which the amount of ethylene (on a molar basis) is 30 percent. During conditioning, the reactor is maintained at a pressure ranging from 255 psig (1860 kPa absolute) to 285 psig (2070 kPa absolute) with a gas hourly space velocity of 6900 $hr^{-1}$. Following conditioning, the feed is switched to all nitrogen, and the reactor is heated to an initial startup temperature of 235° C. Once the initial start-up temperature is reached, the feed gas is switched from all nitrogen to a reactive feed gas composition (on a molar basis) of 30% ethylene, 8% oxygen, 1% carbon dioxide, 0.6% ethane, and 1.8 ppm ethyl chloride. After start-up the temperature is adjusted to achieve a target reactor outlet ethylene oxide concentration of 2 mole %. The resulting efficiency and reaction temperatures are shown in Tables I and II below. The data in Table I are generated by performing the catalyst conditioning method prior to starting-up a fresh catalyst. The data in Table II are generated by performing the catalyst conditioning method on a one month old aged catalyst prior to re-starting the catalyst. The restart conditions are identical to that of the initial startup except ethyl chloride is at 2.25 ppm. After the restart the temperature is either adjusted to achieve a target reactor outlet ethylene oxide concentration of 2 mole % or kept constant at 235° C. In case of operating at a constant reaction temperature of 235° C., the temperature and efficiency equivalent to that at reactor outlet ethylene oxide concentration of 2 mole % are compared. To put the temperature on a common basis, the temperature values are calculated for a common ethylene oxide concentration using a ratio of $\Delta$ temperature/$\Delta$ ethylene oxide concentration of 12.5. To put the efficiency on a common basis, the efficiency values are calculated for a common ethylene oxide concentration using a ratio of $\Delta$ efficiency/$\Delta$ ethylene oxide concentration of –3.

TABLE I

| Run | Conditioning Conditions | Conditioning Temp (T ° C.) | Initial start-up (after 4-5 days) | |
|---|---|---|---|---|
| | | | T(° C.) at 2% EO | % Eff at 2% EO |
| 01 | No conditioning | N/A | 235.0 | 85.9 |
| 02(a) | Ethylene conditioning | 180 | 230.5 | 85.0 |
| 02(b) | Ethylene conditioning | 200 | 232.9 | 85.4 |
| 02(c) | Ethylene conditioning | 220 | 235.0 | 85.3 |
| 03(a) | Nitrogen conditioning | 200 | 235.4 | 85.8 |
| 03(b) | Nitrogen conditioning | 220 | 234.4 | 85.4 |
| 04 | No conditioning and start-up with 2.25 ppm ethyl chloride for 8 hours | N/A | 231.1 | 85.4 |
| 05 | Nitrogen conditioning and start-up with 2.25 ppm ethyl chloride for 8 hours | 220 | 236.9 | 85.0 |

TABLE II

| Run | Conditioning Conditions | Conditioning Temp (T° C.) | Prior to shut down | | 3 days after restart | |
|---|---|---|---|---|---|---|
| | | | T (° C.) at 2% EO | % Eff at 2% EO | T (° C.) at 2% EO | % Eff at 2% EO |
| 01 | No conditioning | N/A | 234.6 | 85.1 | 234.1 | 85.9 |
| 02(a) | Ethylene conditioning | 150 | 239.7 | 85.3 | 236.3 | 86.1 |
| 02(b) | Ethylene conditioning | 180 | 244.5 | 85.3 | 238.4 | 85.6 |
| 03 | Nitrogen conditioning | 150 | 230.5 | 85.2 | 231.2 | 85.8 |
| 04 | Nitrogen conditioning | 220 | 231.0 | 85.4 | 237.3 | 85.6 |

Figure 3:
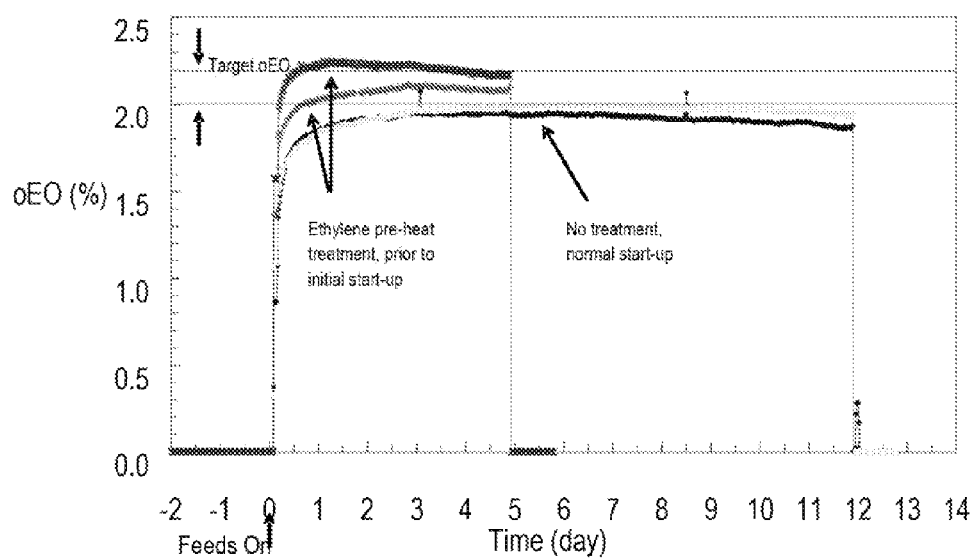
FIG. 3 is a graph depicting the effect of ethylene conditioning on the performance of a high efficiency catalyst.

The post start-up and post-restart temperatures in Tables I and II, respectively, are those required to achieve the target ethylene oxide concentration and are indicative of the catalyst activity. Runs 01 and 02(a) of Table I demonstrate that when exposed to a conditioning feed gas comprising ethylene and nitrogen at a conditioning temperature of 180° C. for 40 hours, the catalyst activity gain is approximately 5° C. The activity increase diminishes as the conditioning temperature is increased to 200° C. and 220° C. The data for duplicate experiments for each of Runs 01 and 02(b) of Table I are graphically displayed in FIG. 3. As the figure indicates, with ethylene/nitrogen conditioning, the target ethylene oxide concentration of 2 mole % is attained in less than 12-16 hours, whereas without conditioning the target value is not attained for 48-72 hours.

In Run 04, the start-up ethyl chloride level was increased to 2.25 ppm for a period of 8 hours without conditioning the catalyst. The target ethylene oxide concentration was attained in a substantially similar time frame in Runs 02(a) and 04 and the runs had similar activation curves. While this result may suggest that organic chloride levels (and Z*) can be increased during start-up to condition the catalyst in lieu of conditioning the catalyst before start-up with a non-reactive conditioning medium, in practice, the latter approach is preferred. Ethylene conditioning can be done prior to start-up while the reactor is heating up and is less likely to compromise the catalyst efficiency than is exposing the catalyst to high initial organic chloride start-up concentrations. In general, the use of increased organic chloride levels to condition the catalyst during start-up requires precise control of Z* and reaction temperature. Due to the array of variables involved in the start-up of a commercial ethylene oxide plant, the likelihood of not attaining the right Z* quickly or of over-chlorinating the high-efficiency catalyst is significant. This, in turn, may lower the catalyst activity and delay activation as well as reduce the catalyst efficiency.

The conditioning processes described herein may be used to improve the performance of a catalyst which is in service by temporarily shutting it down to condition it. A comparison of the pre-shutdown and post-restart temperatures for the various runs in Table II can be made to determine the activity gains or losses incurred by shutting down the process to condition the catalyst. As indicated in Table II, conditioning with ethylene at 150° C. produces an activity gain of 3° C. At a conditioning temperature of 180° C., the activity gain is 6° C. In contrast, when used with a process re-start, conditioning with nitrogen at 150° C. results in almost no activity change, while at 220° C. the penalty increases to 6° C. As shown in Table II, there is a moderate gain in efficiency after shutdown and restart in general. Unlike the strong dependence of activity on the conditioning processes, the gain in selectivity is attributable more to the effects of shutting down and restarting the process. Thus, a poorly performing catalyst can be shutdown and conditioned at temperatures no greater than 180° C. to revive its performance using a non-reactive mixture of ethylene and nitrogen.

EXAMPLE II

Tables III and IV below set forth reactor performance data for shutdowns and restarts of a high efficiency silver catalyst with a rhenium promoter. In the examples described therein, a plurality of tubes are employed, each of which comprises a pilot plant reactor loaded with whole pills of a rhenium-promoted, high efficiency silver catalyst. Except as otherwise indicated below, the epoxidation feed gas composition for the various runs (on a molar basis) is 30-35% ethylene, 0.6% ethane, 5.0 to 8.5% oxygen, and 0.3 to 3.0% carbon dioxide, with the balance being a nitrogen ballast gas (all percentages are based on the total moles of reactor feed gas). The gas hourly space velocity is maintained between 5,900-7,000 $hr^{-1}$, and the work rate is 10 to 15 $lb/ft^3/hr$ (160 to 240 $kg/m^3/hr$). Reaction temperature and efficiency data are normalized based on a 2.0% value of Δ EO % (i.e., change in ethylene oxide concentration in mole percent) wherein Δ EO % is calculated from the reactor inlet and outlet concentrations of ethylene oxide as follows:

$$\text{Shrink Factor (SF)} = (200 + C_{EO\ Inlet})/(200 + C_{EO\ Outlet}). \quad (3)$$

$$\Delta EO\% = SF \cdot C_{EO1} - C_{EO\ Outlet} \quad (4)$$

The "Shrink Factor" represents the net volumetric reduction occurring due to the production of the ethylene oxide. In the case of ethylene oxide production, for every mole of ethylene oxide produced, there is a net reduction of 0.5 moles of total gas resulting in a corresponding reduction in the volumetric flow rate. The epoxidation temperature (as indicated by the reactor coolant inlet temperature) is adjusted to obtain the desired value of Δ EO %, and Z* is set at its optimum (efficiency-maximizing) value at the epoxidation temperature and the selected value of Δ EO %=2.0%.

In Runs 01-07 of Table III, the epoxidation temperature prior to the reactor shutdown is less than 230° C. In Runs 08-13 of Table IV, the epoxidation temperature prior to the reactor shutdown (i.e., prior to the cessation of epoxidation) is greater than 230° C. However, the temperatures shown in the tables may vary from these values because they were normalized to a Δ EO value of =2.0 mole %. Each table identifies the reactor conditions maintained during the shutdown (with the reactor coolant inlet temperature used to indicate the conditioning temperature), the normalized reaction temperature (as indicated by the normalized reactor coolant inlet temperature), the normalized efficiency to ethylene oxide before the shutdown at a ΔEO % of 2.0, and the normalized reaction temperature and efficiency following re-start at a ΔEO % of 2.0. To normalize and put the efficiency on a common basis, the efficiency values are calculated for a common ethylene oxide concentration using a ratio of Δ efficiency/Δ ethylene oxide concentration of −3.

TABLE III

| | | | Reactor Performance | | | | |
| | | | Before Shutdown | | After Restart | | |
| Run | SD ("Shutdown") Catalyst Conditioning Conditions | SD Time (hrs) | T (°C.) | Eff (%) | T (°C.) | Eff (%) | Response |
| --- | --- | --- | --- | --- | --- | --- | --- |
| 01 | Avg. reactor temp of 180° C. Nitrogen conditioning medium at 290 psig (2100 kPa absolute). Catalyst aged 5 days prior to SD. | 38 | 220.3 | 85.9 | 220.1 | 86.9 | 1.0% gain in efficiency without loss of activity. |
| 02 | Avg. reactor temp of 180° C. Nitrogen conditioning medium at 295 psig (2140 kPa absolute). Catalyst aged 15 days prior to shutdown. | 113 | 225.7 | 86.1 | 225.9 | 87.9 | 1.8% gain in efficiency with no loss of activity. |
| 03 | Avg. reactor temp of 220° C. for first 20 hours of SD, followed by avg. reactor temp of 150° C. for 10 hours (remainder of SD). Nitrogen conditioning medium at 275 psig (2000 kPa absolute). Catalyst aged 18 days prior to SD. | 50 | 219.2 | 83.4 | 221.9 | 85.7 | 2.3% gain in efficiency with 2.7° C. activity loss. |
| 04 | Avg. reactor temp of 50° C. Nitrogen conditioning medium at 295 psig (2140 kPa absolute). Catalyst aged 120 days prior to shutdown. | 62 | 224.6 | 87.5 | 224.0 | 88.5 | 1.0% efficiency gain |
| 05 | Avg. reactor temp of 204.6° C. Conditioning medium of 25% (vol.) ethylene and 75% (vol.) nitrogen with 1.1 ppm ethyl chloride. Catalyst age of 43 days prior to SD. | 22 | 227.5 | 88.0 | 231.3 | 88.7 | 0.7% gain in efficiency with 3.8° C. loss in activity. |
| 06 | Avg. reactor temp of 190.6° C. Conditioning medium of 25% (vol.) ethylene and 75% (vol.) nitrogen with 1.2 ppm ethyl chloride. Catalyst age of 22 days prior to SD. | 23 | 227.2 | 86.3 | 231.0 | 87.2 | 0.9% gain in efficiency with 3.1° C. loss in activity. |
| 07 | Avg. reactor temp of 227.1° C. Nitrogen conditioning medium at 295 psig (2140 kPa absolute). Catalyst age of 113 days prior to shutdown. | 18 | 223.6 | 87.2 | 225.5 | 87.9 | 0.7% gain in efficiency with 1.9° C. loss of activity. |

TABLE IV

| Run | SD ("Shutdown") Catalyst Conditioning Conditions | SD Time (hrs) | Before Shutdown T (° C.) | Before Shutdown Eff (%) | After Restart T (° C.) | After Restart Eff (%) | Response |
|---|---|---|---|---|---|---|---|
| 08 | Avg. reactor temp of 110° C. for first 17 hours and 150° C. for remainder of SD period. Nitrogen conditioning medium at 290 psig (2100 kPa absolute). Catalyst age of 50 days prior to SD. | 44 | 232.7 | 88.3 | 233.5 | 88.4 | Re-start at similar efficiency with activity loss within the error of measurement |
| 09 | Avg. reactor temp of 200.7° C. Conditioning medium of 25% ethylene (vol) and 75% (vol) nitrogen with 4.3 ppm ethyl chloride. Catalyst age of 147 days prior to SD. | 22 | 234.6 | 87.0 | 234.2 | 87.0 | Similar performance before and after re-start |
| 10 | Avg. reactor temp of 150° C. Nitrogen conditioning medium at 260 psig (1890 kPa absolute). Catalyst age of 164 days prior to SD. | 84 | 234.6 | 88.3 | 234.8 | 88.5 | Similar performance before and after re-start |
| 11 | Avg. reactor temp of 25.4° C. for first 106 hours with nitrogen blanketing but without nitrogen purge and 120° C. for remainder of SD with nitrogen conditioning medium at 275 psig (2000 kPa absolute). Catalyst age of 200 days prior to SD. | 144 | 235.6 | 88.3 | 236.2 | 87.9 | Differences between efficiency and activity before and after re-start are within measurement error. |
| 12 | Avg. reactor temp of 205.0° C. Nitrogen conditioning medium at 300 psig (2170 kPa). Catalyst age of 59 days at SD. | 138 | 232.2 | 88.5 | 233.6 | 88.6 | 1.4° C. loss in activity with negligible efficiency change. |
| 13 | Avg. reactor temp of 233.5° C. Nitrogen conditioning medium at 295 psig (2140 kPa absolute). Catalyst age of 176 days at SD. | 19 | 228.7 | 87.6 | 233.8 | 87.7 | 5.1° C. loss in activity with negligible efficiency change. |

As Table III data indicates, the use of a conditioning temperature of less than 180° C. improves the efficiency of the epoxidation process operated below 230° C. without incurring an activity penalty when a nitrogen conditioning medium is used. Conversely, when conditioning temperatures in excess of 180° C. are used, activity losses of 2° C. or greater are incurred. The data presented in Table IV indicate that the use of conditioning temperatures of 180° C. or less prevents losses in performance upon re-start when the epoxidation temperature is over 230° C. and when a nitrogen conditioning medium is used. Thus, the catalyst conditioning methods described herein enhance the performance of high-efficiency, silver catalysts in the production of ethylene oxides.

EXAMPLE III

A pilot plant reactor is charged with whole pills of a high efficiency, silver ethylene oxide catalyst containing a promoting amount of rhenium. A pilot plant reactor has a volume of 0.087 ft$^3$. The catalysts are conditioned by introducing a conditioning feed gas mixture of ethylene and nitrogen in which the amount of ethylene is 16 percent or lower. During conditioning, the reactor is maintained at a pressure of 290 psig (2100 kPa absolute) with the total feed gas flow rate of 430-435 standard cubic feet (12.2-12.3 standard cubic meters) per hour. For catalyst conditioning, the conditioning temperature is at 180° C. for a conditioning period of 19 hours or less prior to an initial start-up of the reactor. Following conditioning, the initial start-up feed gas composition (on a mole percent basis) is 30-35% ethylene, 8.2% oxygen, 1.1-1.6% carbon dioxide, 0.6% ethane, and 1.8-2.0 ppmv ethyl chloride. During the start-up the temperature is adjusted to achieve a target ethylene oxide concentration of 2 mole % of the reaction product. The resulting efficiency and reaction temperatures are shown in Table V below. The data in Table V are generated by performing the catalyst conditioning method prior to starting-up a fresh catalyst. The temperatures in column 4 of Table V are those required to achieve the target ethylene oxide concentration and are indicative of catalyst activity. Runs A01, A02 and A 03 of Table V demonstrate that when exposed to a conditioning feed gas comprising ethylene and nitrogen at a conditioning temperature of 180° C. for at least 16 hours, the catalyst activity gain is approximately 7° C.

TABLE V

| Run | Conditioning Conditions | Conditioning Temp (T ° C.) | Start-up (after 4-5 days) | |
|---|---|---|---|---|
| | | | T(° C.) at 2% EO | % Eff at 2% ΔEO |
| A 01 | No conditioning | N/A | 227 | 86.1 |
| A 02 | 13% Ethylene conditioning for 19 hours | 180 | 220 | 86.0 |
| A 03 | 16% Ethylene conditioning for 16 hours | 180 | 219 | 85.9 |

EXAMPLE IV

A continuously stirred tank reactor ("CSTR") is loaded with whole pills of a high-efficiency ethylene oxide catalyst containing a promoting amount of rhenium. For the comparative study, the reactor is directly heated up from room temperature to an initial startup temperature of 235° C. under nitrogen flow. For the ethylene conditioning, the reactor is heated up from room temperature to 180° C. under nitrogen flow. At 180° C., the feed gas is switched from all nitrogen to a conditioning feed gas mixture that contains 30 percent ethylene (on a molar basis) in nitrogen. During the conditioning and the entire time of the reaction runs, the reactor is maintained at 285 psig (2070 kPa absolute) with a gas hourly space velocity of 8600 hr$^{-1}$. Following 4 hours of conditioning at 180° C., the reactor is heated to an initial startup temperature of 235° C. under the same conditioning feed gas mixture. Once the initial start-up temperature is reached, the feed gas is switched from all nitrogen (in the case of comparative study) or the 30 mole percent ethylene in nitrogen (in the case of ethylene conditioning) to a reactive feed gas composition (on a molar basis) of 30% ethylene, 8% oxygen, 1% carbon dioxide, 0.56% ethane, and 1.75 ppm ethyl chloride. The resulting efficiency and reactor delta EO (mole percent) are shown in Table VI below.

TABLE VI

| Conditioning Conditions | Conditioning Temp (T ° C.) | Average Performance | | | |
|---|---|---|---|---|---|
| | | Day 1 | | Day 4 | |
| | | % dEO | % Eff | % dEO | % Eff |
| No conditioning | N/A | 1.57 | 85.0 | 1.60 | 84.9 |
| 30% Ethylene conditioning, 4 hours | 180 | 1.69 | 84.2 | 1.67 | 85.0 |

Figure 4:
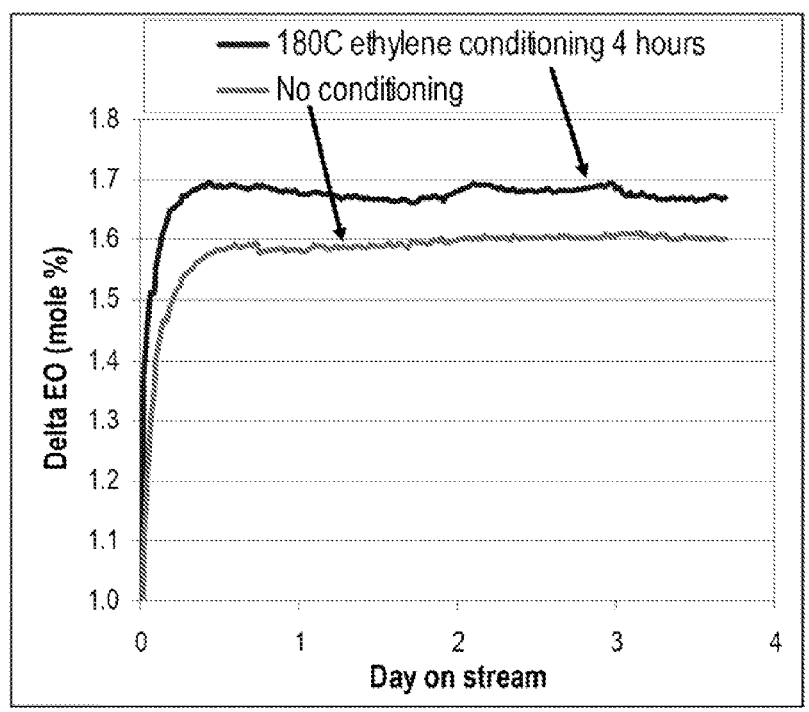
FIG. 4 is a graph depicting the effect of ethylene conditioning for a four hour conditioning period on the performance of a high-efficiency catalyst.

The results demonstrate that when exposed to a conditioning feed gas comprising ethylene and nitrogen at a conditioning temperature of 180° C. for 4 hours, the catalyst activity is higher than in the absence of conditioning. The corresponding catalyst workrate at day 4 after initial startup is 270.5 kg/m$^3$/hr for the catalyst without conditioning and is 282.8 kg/m$^3$/hr for the catalyst with 4 hours conditioning with 30% ethylene at 180° C. The activity data of the above runs are graphically displayed in FIG. 4. As the figure indicates, with ethylene/nitrogen conditioning, the high-efficiency catalyst activates faster and its activity stays higher.

The invention claimed is:

1. A process for conditioning a high efficiency silver catalyst used to manufacture ethylene oxide by reacting ethylene, oxygen, and at least one organic chloride over the catalyst, the conditioning process comprising the steps of:
    introducing a feed gas to the high efficiency silver catalyst at one or more conditioning temperatures ranging from 150° C. to 180° C. for a selected period of time, wherein the selected period of time is at least 4 hours, and the feed gas comprises at least one component selected from the group consisting of ethylene, methane, and nitrogen, and the introducing step occurs such that the catalyst is not simultaneously exposed to ethylene and oxygen during the selected period of time.

2. The process for conditioning a high efficiency silver catalyst of claim 1, wherein the high efficiency silver catalyst is a fresh catalyst.

3. The process for conditioning a high-efficiency silver catalyst of claim 1, wherein the selected period of time is at least 12 hours.

4. The process for conditioning a high-efficiency silver catalyst of claim 1, wherein the selected period of time is no greater than 200 hours.

5. The process for conditioning a high-efficiency silver catalyst of claim 1, wherein the at least one component is ethylene and nitrogen.

6. The process for conditioning a high-efficiency silver catalyst of claim 1, wherein the at least one component is nitrogen.

7. The process for conditioning a high-efficiency silver catalyst of claim 1, wherein the high-efficiency silver catalyst is an aged catalyst.

8. The process for conditioning a high-efficiency silver catalyst of claim 1, wherein the high-efficiency silver catalyst is aged an amount no greater than 1.1 kt ethylene oxide/cubic meter of the high-efficiency silver catalyst.

9. A process for manufacturing ethylene oxide by reacting ethylene, oxygen, and at least one organic chloride over a high-efficiency silver catalyst to yield a product comprising ethylene oxide, the process comprising:
    performing the process for conditioning a high efficiency catalyst of claim 1, wherein the feed gas is a first feed gas; and introducing a second feed gas to the high efficiency silver catalyst, wherein the second feed gas comprises ethylene, oxygen, and the at least one organic chloride, and the ethylene and the oxygen react to form the ethylene oxide.

10. The process for manufacturing ethylene oxide of claim 9, wherein the second feed gas is introduced to the high efficiency silver catalyst at a reaction temperature of no less than 210° C.

11. The process for manufacturing ethylene oxide of claim 9, wherein the step of introducing the first feed gas to the high efficiency silver catalyst follows a reactor shutdown.

12. The process manufacturing ethylene oxide of claim 9, wherein the step of introducing the first feed gas to the high efficiency silver catalyst follows the occurrence of reactor trip condition.

13. The process for manufacturing ethylene oxide of claim 9, wherein the step of introducing the second feed gas to the high efficiency silver catalyst is performed before the step of introducing the first feed gas to the high efficiency silver catalyst.

14. The process for manufacturing ethylene oxide of claim 9, wherein the step of introducing the second feed gas to the high efficiency silver catalyst is performed after the step of introducing the first feed gas to the high efficiency silver catalyst.

15. The process for manufacturing ethylene oxide of claim 9, wherein the step of introducing a second feed gas to the high efficiency silver catalyst comprises introducing the second feed gas at a reaction temperature ranging from 220° C. to 280° C., ethylene is present in an amount ranging from 15 mole percent to 35 mole percent of the second feed gas, and oxygen is present in an amount ranging from 5 mole percent to 10 mole percent of the second feed gas.

* * * * *